(12) United States Patent
Komatsu et al.

(10) Patent No.: US 8,758,685 B2
(45) Date of Patent: Jun. 24, 2014

(54) AUTOMATIC ANALYZER AND OPERATING METHOD FOR SAME

(75) Inventors: Hidenobu Komatsu, Hitachinaka (JP); Tetsuya Fujisawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 788 days.

(21) Appl. No.: 12/207,022

(22) Filed: Sep. 9, 2008

(65) Prior Publication Data

US 2009/0068748 A1     Mar. 12, 2009

(30) Foreign Application Priority Data

Sep. 10, 2007   (JP) .................. 2007-234155

(51) Int. Cl.
*G01N 21/00* (2006.01)
*G01N 35/00* (2006.01)
*G01N 35/02* (2006.01)

(52) U.S. Cl.
USPC .................. 422/67; 422/63; 436/43; 436/50

(58) Field of Classification Search
USPC ................... 422/63, 67; 436/43, 50
See application file for complete search history.

(56) References Cited

U.S. PATENT DOCUMENTS

| 4,774,055 A * | 9/1988 | Wakatake et al. ............... 422/64 |
| 5,876,668 A | 3/1999 | Kawashima et al. |
| 6,709,634 B1 | 3/2004 | Okada et al. |
| 2002/0031837 A1 | 3/2002 | Matsubara et al. |

FOREIGN PATENT DOCUMENTS

| JP | 62-228935 A | 10/1987 |
| JP | 63-24164 A | 2/1988 |
| JP | 8-194004 | 7/1996 |

* cited by examiner

*Primary Examiner* — Dean Kwak
(74) *Attorney, Agent, or Firm* — Mattingly & Malur, PC

(57) ABSTRACT

An automatic analyzer is free from limitations on layout of various mechanisms, and thus causing no bottlenecks, for example, in a space-saving design of the automatic analyzer. This invention includes a coaxial planar duplex arrangement of two dilution disks each with annularly disposed dilution cells, and the dilution disks A and B operate independently of each other. Various mechanisms (parent-sample sampling mechanism, diluent delivery mechanism, diluent/sample mixing mechanism, and diluted-sample sampling mechanism) used in a dilution process can each access the two dilution disks. The dilution process for a parent sample, executed on the dilution disks A and B, can be continuously conducted by providing a fixed delay in operational timing between the two dilution disks.

2 Claims, 2 Drawing Sheets

AUTOMATIC ANALYZER AND OPERATING METHOD FOR SAME

BACKGROUND OF THE INVENTION

1. Field of the Invention

The present invention relates generally to automatic analyzers for clinical laboratory tests, and to methods of operating such an automatic analyzer. More particularly, the invention is directed to diluting a parent sample.

2. Description of the Related Art

In automatic analyzers for clinical laboratory tests, reduction in the amount of reaction liquid to be used for analysis is required for reduction in running costs associated with laboratory tests. The amount of reaction liquid is proportional to the amount of sample to be used for the analysis. To reduce the amount of reaction liquid, therefore, it is absolutely necessary that the amount of sample be reduced to a very small level. At the current technical level of sampling, however, significant reduction in the amount of reaction liquid is difficult since quantitative minimization of sampling has its limit.

Accordingly, microsampling generally uses sample dilution. JP-A-08-194004 proposes a method of diluting a sample.

SUMMARY OF THE INVENTION

The dilution of a sample usually uses a dilution disk.

The dilution disk with an annular array of dilution cells rotates in single-step feed mode, and the distance through which the disk moves in one rotation is equivalent to a number without a common factor with respect to the total number of dilution cells present on the disk.

When the dilution disk repeating the above rotation is in a stopped condition, various mechanisms that access the dilution disk (namely, a parent-sample sampling mechanism, a diluent delivery mechanism, a mixing mechanism, and a diluted-sample sampling mechanism) conduct a parent-sample dilution process (parent-sample sampling, diluent delivery, diluent/sample mixing, and diluted-sample sampling).

During the sample dilution process based on this scheme, however, the dilution disk rotates with the above-defined number as its single-step feed rate. That is to say, the above four mechanisms (the parent-sample pipetting mechanism, the diluent delivery mechanism, the mixing mechanism, and the diluted-sample pipetting mechanism) perform the respective functions during the stopped state of the dilution disk.

This means that the layout of each mechanism which accesses the dilution disk is limited, which, in turn, may cause bottlenecks, for example, in the space-saving design of the analyzer.

With the above problem taken into account, the present invention has an object to provide an automatic analyzer free from limitations on layout of various mechanisms, and thus causing no bottlenecks, for example, in a space-saving design of the automatic analyzer.

An aspect of the present invention, an automatic analyzer comprises: a sample array storage unit including a sample disk on which parent sample containers each for accommodating a parent sample are arrayed; a reaction disk with reaction cells arrayed thereon; a dilution disk with dilution cells annularly arrayed thereon; a parent-sample sampling mechanism for pipetting each parent sample from the sample array storage unit into each dilution cell; a diluent delivery mechanism for delivering a liquid diluent to the dilution cell having the parent sample pipetted thereinto; a mixing mechanism for mixing the pipetted parent sample and the diluent; a diluted-sample sampling mechanism for pipetting into one of the reaction cells a diluted sample created by mixing the parent sample and the diluent in the dilution cell; and control means that conducts operational control of the above-described types of disks and mechanisms; wherein the control means uses a control function to ensure that successive actions in a dilution process for the parent sample, that is, parent-sample sampling, diluent delivery, diluent/sample mixing, and diluted-sample sampling are sequentially conducted for one arbitrarily selected dilution cell on the dilution disk.

In the dilution process for the parent sample, therefore, each mechanism can freely determine an access position with respect to the dilution disk because of no limitations on the rotation of the disk.

In another aspect of the present invention, two dilution disks constructed to rotate concentrically about a common axis are arranged in two rows, one to form an inner peripheral region and the other to form an outer peripheral region, and the two dilution disks operate independently of each other.

In yet another aspect of the present invention, various mechanisms that are used in a dilution process for a parent sample (namely, a parent-sample sampling mechanism, a diluent delivery mechanism, a mixing mechanism, and a diluted-sample sampling mechanism) are each disposed to be able to access two dilution disks, and are each constructed to move dilution cells to accessible positions according to particular rotational movements of the dilution disks and sequentially conduct the dilution process in each dilution cell.

In a further aspect of the present invention, when two dilution disks exist, successive actions in a dilution process for a parent sample, that is, parent-sample sampling, diluent delivery, diluent/sample mixing, and diluted-sample sampling are sequentially conducted using one arbitrarily selected dilution cell on each dilution disk. After the dilution process using the arbitrarily selected dilution cell, the associated dilution disk rotates and the next dilution process using a dilution cell located next to the selected one is started.

The dilution process for the parent sample is executed with a definite delay in operational timing between the two dilution disks. While the diluted sample is being pipetted using one dilution disk A, parent-sample sampling, diluent delivery, and diluent/sample mixing are executed using other dilution disk B. After diluted-sample sampling on the dilution disk A, the pipetting action immediately changes to diluted-sample sampling on the dilution disk B.

Since the execution timing of the dilution process is delayed between the two dilution disks in this manner, the parent sample can be diluted efficiently and continuously.

According to the present invention, because of no limitations on the rotation of the dilution disk(s), each of the parent-sample sampling mechanism, diluent delivery mechanism, diluent/sample mixing mechanism, and diluted-sample sampling mechanism used in the dilution process for the parent sample can freely determine an access position with respect to the dilution disk(s). Flexibility of the layout of each mechanism improves, which is very beneficial for design purposes such as apparatus space saving.

DESCRIPTION OF THE PREFERRED EMBODIMENTS

Embodiments of the present invention will be described in detail, pursuant to FIGS. 1 and 2.

A first embodiment of the present invention is described below.

Figure 1:
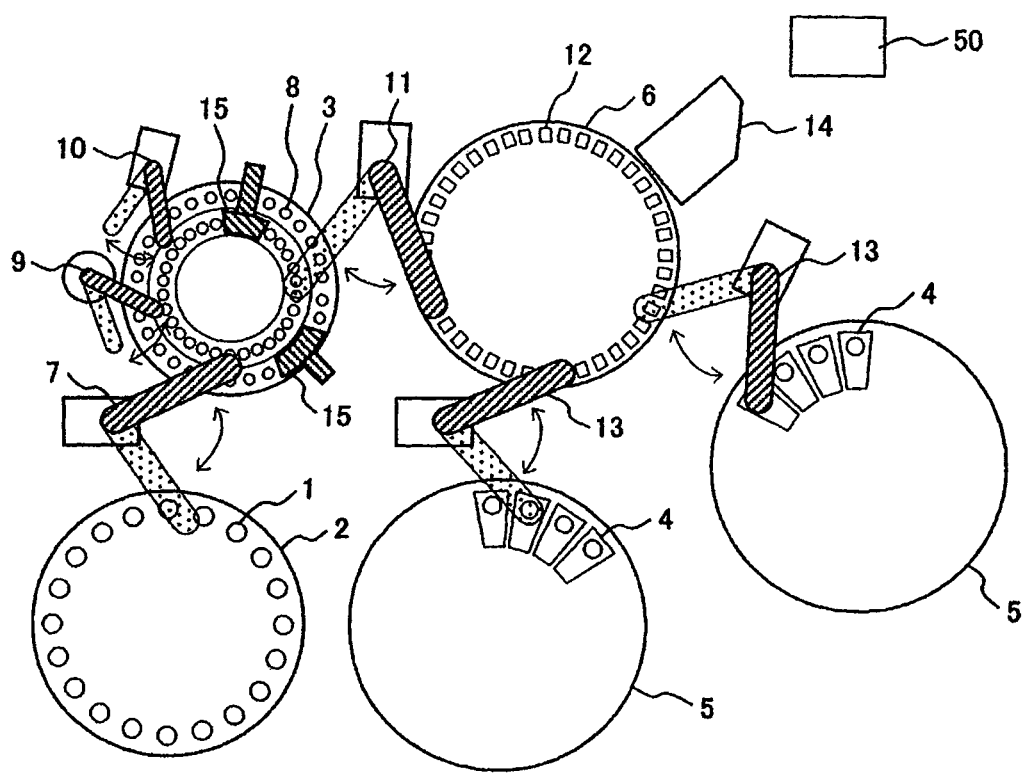
FIG. 1 is a diagram relating to an embodiment of the present invention, illustrating the overall configuration of an automatic analyzer for clinical laboratory tests.

FIG. 1 is a total apparatus block diagram of a biochemical automatic analyzer used in the present invention.

The automatic analyzer has a sample disk 2 (sample array storage unit) for accommodating parent samples 1 that were taken into test tubes or the like, a dilution disk 3 for diluting the parent samples 1, a reagent coolbox 5 for cold storage of reagent bottles 4, and a reaction disk 6 for causing a reaction of a reaction liquid while rotating cyclically at fixed intervals.

Each parent sample 1 is suctioned by a parent-sample sampling mechanism 7 and then pipetted into any one of dilution cells 8 arrayed on the dilution disk 3. A liquid diluent is delivered from a diluent delivery mechanism 9 to the dilution cell 8 into which the parent sample 1 has been pipetted, and the parent sample and the diluent are stirred and mixed by a diluent/sample mixing mechanism 10. The sample that has been diluted on the dilution disk 3 is suctioned by the diluted sample sampling mechanism 11 and then pipetted into any one of reaction cells 12 arrayed on the reaction disk 6.

A reagent is added to the diluted sample by a suctioning action of a reagent-sampling mechanism 13 from one of the reagent bottles 4, and after the diluted sample and the reagent have been made to react in the reaction cell 12, absorbance is measured with a spectrophotometer 14. Measured data is collected into a computer 50 (a controller), and analytical results are output therefrom. The dilution cell 8 is cleaned by a cleaning mechanism 15 and later reused.

The computer 50 (controller) is used to control the operation of the above-described types of disks and mechanisms. The computer 50 uses a control function to ensure that in the dilution process for the parent sample, successive actions of parent-sample sampling, diluent delivery, diluent/sample mixing, and diluted-sample sampling are sequentially conducted for one arbitrarily selected dilution cell on the dilution disk.

According to the above control function, each of the parent-sample sampling mechanism, diluent delivery mechanism, diluent/sample mixing mechanism, and diluted-sample sampling mechanism used in the dilution process for the parent sample can freely determine an access position with respect to the dilution disk because of no limitations on rotation thereof. Each mechanism improves in flexibility of lay-out, and this improvement becomes very beneficial for design purposes such as apparatus space saving.

The controller also has a control function that controls the operation of each type of disk and each kind of mechanism so that after the dilution of the parent sample using one dilution cell, the dilution disk rotates and the next dilution process using a dilution cell located next to that dilution cell is conducted.

In this way, the dilution process that uses dilution cells is repeated for each cell in sequential feed mode, so the rotation of the dilution disk through one full turn allows all cells to be used and operation to be controlled easily.

Figure 2:
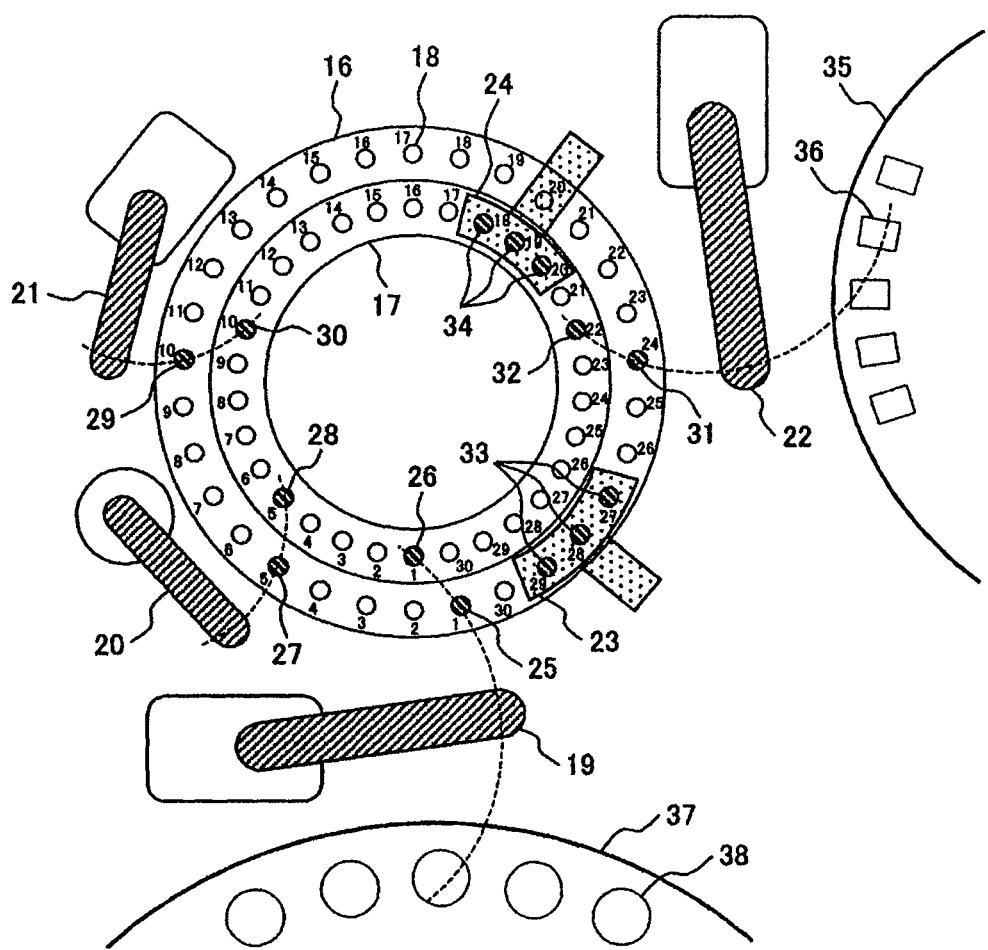
FIG. 2 is a diagram relating to the embodiment of the present invention, illustrating in detail the configuration concerned with a dilution process for a parent sample.

FIG. 2 is a detailed diagram illustrating the dilution process for the parent sample.

Two dilution disks that rotate concentrically about a common axis are arranged in two rows, one to form an inner peripheral region and the other to form an outer peripheral region, and the two dilution disks can operate independently of each other. Dilution cells 18 are arrayed annularly on the dilution disk A 16 and the dilution disk B 17.

An example in which a total number of dilution cells present on the two dilution disks is 60 (30 each) is described below.

A parent-sample sampling mechanism 19, a diluent delivery mechanism 20, a diluent/sample mixing mechanism 21, a diluted-sample sampling mechanism 22, and a dilution cell cleaning mechanism A 23 and a dilution cell cleaning mechanism B 24 access the two dilution disks at a parent-sample pipetting position A 25 and parent-sample pipetting position B 26, a diluent delivery position A 27 and a diluent delivery position B 28, a diluent/sample mixing position A 29 and a diluent/sample mixing position B 30, a diluted-sample suction position A 31 and a diluted-sample suction position B 32, and a dilution cell cleaning position A 33 and a dilution cell cleaning position B 34, respectively. These access positions are shown in FIG. 2. The dilution disks rotate to move the dilution cells 18 to each position for dilution.

The two dilution disks are arranged within a spatial range over which successive actions of each mechanism extend. Thus, one particular mechanism can access the two dilution disks. Also, this arrangement of the dilution disks makes it unnecessary to provide independent mechanisms for each dilution disk, and hence simplifies the configuration of the apparatus.

In addition, since the two dilution disks rotate independently of each other, operation of each kind of mechanism can be executed for each dilution disk. Thus, a total processing time can be reduced since, while one dilution disk is being used for sampling the diluted sample, the other dilution disk can be used to execute parent-sample sampling, diluent delivery, and diluent/sample mixing.

Furthermore, since the two dilution disks are arranged to rotate concentrically about a common axis are arranged planarly in two rows, one to form an inner peripheral region and the other to form an outer peripheral region, the layout of the dilution disks, compared with separate layout of each, is compact and convenient for configuring the apparatus such that one mechanism accesses the two dilution disks.

Tables 1 and 2 list actions of each mechanism for the dilution disk A 16 and the dilution disk B 17 shown in FIG. 2.

TABLE 1

| | Access position | Dilution process | No. of cycles | | | | | | | |
|---|---|---|---|---|---|---|---|---|---|---|
| | | | 1 | | 2 | | 3 | | 4 | .. |
| Dilution disk A | 1 | Parent sample pipetting position A | Parent sample sampling | 1-A | | 27-A | 22-A | 8-A | | 8-A | |
| | 2 | | | 2-A | | 28-A | 23-A | 9-A | | 9-A | |
| | 3 | | | 3-A | | 29-A | 24-A | 10-A | | 10-A | |
| | 4 | | | 4-A | | 30-A | 25-A | 11-A | | 11-A | |
| | 5 | Diluent delivery position A | Diluent delivery | 5-A | | 1-A | 26-A | 12-A | | 12-A | |
| | 6 | | | 6-A | | 2-A | 27-A | 13-A | | 13-A | |
| | 7 | | | 7-A | | 3-A | 28-A | 14-A | | 14-A | |
| | 8 | | | 8-A | | 4-A | 29-A | 15-A | | 15-A | |
| | 9 | | | 9-A | | 5-A | 30-A | 16-A | | 16-A | |
| | 10 | Diluent/ sample mixing position A | Diluent/ sample mixing | 10-A | | 6-A | 1-A | 17-A | | 17-A | |
| | 11 | | | 11-A | | 7-A | 2-A | 18-A | | 18-A | |
| | 12 | | | 12-A | | 8-A | 3-A | 19-A | | 19-A | |
| | 13 | | | 13-A | | 9-A | 4-A | 20-A | | 20-A | |
| | 14 | | | 14-A | | 10-A | 5-A | 21-A | | 21-A | |
| | 15 | | | 15-A | | 11-A | 6-A | 22-A | | 22-A | |
| | 16 | | | 16-A | | 12-A | 7-A | 23-A | | 23-A | |
| | 17 | | | 17-A | | 13-A | 8-A | 24-A | | 24-A | |
| | 18 | | | 18-A | | 14-A | 9-A | 25-A | | 25-A | |
| | 19 | | | 19-A | | 15-A | 10-A | 26-A | | 26-A | |
| | 20 | | | 20-A | | 16-A | 11-A | 27-A | | 27-A | |
| | 21 | | | 21-A | | 17-A | 12-A | 28-A | | 28-A | |
| | 22 | | | 22-A | | 18-A | 13-A | 29-A | | 29-A | |
| | 23 | | | 23-A | | 19-A | 14-A | 30-A | | 30-A | |
| | 24 | Diluted sample suction position A | Diluted sample sampling | 24-A | | 20-A | 15-A | 1-A | | 1-A | |
| | 25 | | | 25-A | | 21-A | 16-A | 2-A | | 2-A | |
| | 26 | | | 26-A | | 22-A | 17-A | 3-A | | 3-A | |
| | 27 | Dilution cell cleaning position A | Dilution cell cleaning 1 | 27-A | | 23-A | 18-A | 4-A | | 4-A | |
| | 28 | | Dilution cell cleaning 2 | 28-A | | 24-A | 19-A | 5-A | | 5-A | |
| | 29 | | Dilution cell cleaning 3 | 29-A | | 25-A | 20-A | 6-A | | 6-A | |
| | 30 | | | 30-A | | 26-A | 21-A | 7-A | | 7-A | |

TABLE 1-continued

| | | | | | | | | | | | | | | |
|---|---|---|---|---|---|---|---|---|---|---|---|---|---|---|
| Dilution disk B | 1 | parent sample pipetting position B | Parent sample sampling | | | | | | | 1-B | | 27-B | | 22-B | |
| | 2 | | | | | | | | | 2-B | | 28-B | | 23-B | |
| | 3 | | | | | | | | | 3-B | | 29-B | | 24-B | |
| | 4 | | | | | | | | | 4-B | | 30-B | | 25-B | |
| | 5 | Diluent delivery position B | Diluent delivery | | | | | | | 5-B | | 1-B | | 26-B | |
| | 6 | | | | | | | | | 6-B | | 2-B | | 27-B | |
| | 7 | | | | | | | | | 7-B | | 3-B | | 28-B | |
| | 8 | | | | | | | | | 8-B | | 4-B | | 29-B | |
| | 9 | | | | | | | | | 9-B | | 5-B | | 30-B | |
| | 10 | Diluent/sample mixing position B | Diluent/sample mixing | | | | | | | 10-B | | 6-B | | 1-B | |
| | 11 | | | | | | | | | 11-B | | 7-B | | 2-B | |
| | 12 | | | | | | | | | 12-B | | 8-B | | 3-B | |
| | 13 | | | | | | | | | 13-B | | 9-B | | 4-B | |
| | 14 | | | | | | | | | 14-B | | 10-B | | 5-B | |
| | 15 | | | | | | | | | 15-B | | 11-B | | 6-B | |
| | 16 | | | | | | | | | 16-B | | 12-B | | 7-B | |
| | 17 | | | | | | | | | 17-B | | 13-B | | 8-B | |
| | 18 | Dilution cell cleaning position B | Dilution cell cleaning 1 | | | | | | | 18-B | | 14-B | | 9-B | |
| | 19 | | Dilution cell cleaning 2 | | | | | | | 19-B | | 15-B | | 10-B | |
| | 20 | | Dilution cell cleaning 3 | | | | | | | 20-B | | 16-B | | 11-B | |
| | 21 | | | | | | | | | 21-B | | 17-B | | 12-B | |
| | 22 | Diluted sample suction position B | Diluted sample sampling | | | | | | | 22-B | | 18-B | | 13-B | |
| | 23 | | | | | | | | | 23-B | | 19-B | | 14-B | |
| | 24 | | | | | | | | | 24-B | | 20-B | | 15-B | |
| | 25 | | | | | | | | | 25-B | | 21-B | | 16-B | |
| | 26 | | | | | | | | | 26-B | | 22-B | | 17-B | |
| | 27 | | | | | | | | | 27-B | | 23-B | | 18-B | |
| | 28 | | | | | | | | | 28-B | | 24-B | | 19-B | |
| | 29 | | | | | | | | | 29-B | | 25-B | | 20-B | |
| | 30 | | | | | | | | | 30-B | | 26-B | | 21-B | |

TABLE 2

| | Access position | Dilution process | No. of cylces | | | |
|---|---|---|---|---|---|---|
| | | | 5 | 6 | 7 | 8 |
| Dilution disk A | 1 | Parent sample pipetting position A | Parent sample sampling | 30-A | 26-A | 21-A | 7-A | 7-A |
| | 2 | | | 1-A | 27-A | 22-A | 8-A | 8-A |
| | 3 | | | 2-A | 28-A | 23-A | 9-A | 9-A |
| | 4 | | | 3-A | 29-A | 24-A | 10-A | 10-A |
| | 5 | Diluent delivery position A | Diluent delivery | 4-A | 30-A | 25-A | 11-A | 11-A |
| | 6 | | | 5-A | 1-A | 26-A | 12-A | 12-A |
| | 7 | | | 6-A | 2-A | 27-A | 13-A | 13-A |
| | 8 | | | 7-A | 3-A | 28-A | 14-A | 14-A |
| | 9 | | | 8-A | 4-A | 29-A | 15-A | 15-A |
| | 10 | Diluent/sample mixing position A | Diluent/sample mixing | 9-A | 5-A | 30-A | 16-A | 16-A |
| | 11 | | | 10-A | 6-A | 1-A | 17-A | 17-A |
| | 12 | | | 11-A | 7-A | 2-A | 18-A | 18-A |
| | 13 | | | 12-A | 8-A | 3-A | 19-A | 19-A |
| | 14 | | | 13-A | 9-A | 4-A | 20-A | 20-A |
| | 15 | | | 14-A | 10-A | 5-A | 21-A | 21-A |
| | 16 | | | 15-A | 11-A | 6-A | 22-A | 22-A |
| | 17 | | | 16-A | 12-A | 7-A | 23-A | 23-A |
| | 18 | | | 17-A | 13-A | 8-A | 24-A | 24-A |
| | 19 | | | 18-A | 14-A | 9-A | 25-A | 25-A |
| | 20 | | | 19-A | 15-A | 10-A | 26-A | 26-A |
| | 21 | | | 20-A | 16-A | 11-A | 27-A | 27-A |
| | 22 | | | 21-A | 17-A | 12-A | 28-A | 28-A |
| | 23 | | | 22-A | 18-A | 13-A | 29-A | 29-A |
| | 24 | Diluted sample suction position A | Diluted sample sampling | 23-A | 19-A | 14-A | 30-A | 30-A |
| | 25 | | | 24-A | 20-A | 15-A | 1-A | 1-A |
| | 26 | | | 25-A | 21-A | 16-A | 2-A | 2-A |
| | 27 | Dilution cell cleaning position A | Dilution cell cleaning 1 | 26-A | 22-A | 17-A | 3-A | 3-A |
| | 28 | | Dilution cell cleaning 2 | 27-A | 23-A | 18-A | 4-A | 4-A |
| | 29 | | Dilution cell cleaning 3 | 28-A | 24-A | 19-A | 5-A | 5-A |
| | 30 | | | 29-A | 25-A | 20-A | 6-A | 6-A |

TABLE 2-continued

| Dilution disk B | | | | | | | | | | | |
|---|---|---|---|---|---|---|---|---|---|---|---|
| | 1 | Parent sample pipetting position B | Parent sample sampling | 10-B | | 10-B | | 30-B | 26-B | 21-B | |
| | 2 | | | 11-B | | 11-B | | 1-B | 27-B | 22-B | |
| | 3 | | | 12-B | | 12-B | | 2-B | 28-B | 23-B | |
| | 4 | | | 13-B | | 13-B | | 3-B | 29-B | 24-B | |
| | 5 | Diluent delivery position B | Diluent delivery | 14-B | | 14-B | | 4-B | 30-B | 25-B | |
| | 6 | | | 15-B | | 15-B | | 5-B | 1-B | 26-B | |
| | 7 | | | 16-B | | 16-B | | 6-B | 2-B | 27-B | |
| | 8 | | | 17-B | | 17-B | | 7-B | 3-B | 28-B | |
| | 9 | | | 18-B | | 18-B | | 8-B | 4-B | 29-B | |
| | 10 | Diluent/ sample mixing position B | Diluent/ sample mixing | 19-B | | 19-B | | 9-B | 5-B | 30-B | |
| | 11 | | | 20-B | | 20-B | | 10-B | 6-B | 1-B | |
| | 12 | | | 21-B | | 21-B | | 11-B | 7-B | 2-B | |
| | 13 | | | 22-B | | 22-B | | 12-B | 8-B | 3-B | |
| | 14 | | | 23-B | | 23-B | | 13-B | 9-B | 4-B | |
| | 15 | | | 24-B | | 24-B | | 14-B | 10-B | 5-B | |
| | 16 | | | 25-B | | 25-B | | 15-B | 11-B | 6-B | |
| | 17 | | | 26-B | | 26-B | | 16-B | 12-B | 7-B | |
| | 18 | Dilution cell cleaning position B | Dilution cell cleaning 1 | 27-B | | 27-B | | 17-B | 13-B | 8-B | |
| | 19 | | Dilution cell cleaning 2 | 28-B | | 28-B | | 18-B | 14-B | 9-B | |
| | 20 | | Dilution cell cleaning 3 | 29-B | | 29-B | | 19-B | 15-B | 10-B | |
| | 21 | | | 30-B | | 30-B | | 20-B | 16-B | 11-B | |
| | 22 | Diluted sample suction position B | Diluted sample sampling | 1-B | | 1-B | | 21-B | 17-B | 12-B | |
| | 23 | | | 2-B | | 2-B | | 22-B | 18-B | 13-B | |
| | 24 | | | 3-B | | 3-B | | 23-B | 19-B | 14-B | |
| | 25 | | | 4-B | | 4-B | | 24-B | 20-B | 15-B | |
| | 26 | | | 5-B | | 5-B | | 25-B | 21-B | 16-B | |
| | 27 | | | 6-B | | 6-B | | 26-B | 22-B | 17-B | |
| | 28 | | | 7-B | | 7-B | | 27-B | 23-B | 18-B | |
| | 29 | | | 8-B | | 8-B | | 28-B | 24-B | 19-B | |
| | 30 | | | 9-B | | 9-B | | 29-B | 25-B | 20-B | |

Hyphenated numerals in the table (i.e., 1-A to 30-A, 1-B to 30-B) denote designation numbers of the dilution cells present on the two dilution disks (for convenience' sake, these numbers are simply shown as 1 to 30 in FIG. 1). The dilution process is conducted at positions listed in a boldface box in the table. This table assumes one-sample two-item analysis, in which analysis the pipetting of one diluted sample into a reaction cell 36 is repeated twice.

The dilution process for the parent sample includes four actions controlled by a control function of a computer 50 (controller). The four actions are listed below.

(1) Parent-Sample Sampling Action

A parent sample 38 is suctioned from a sample disk 37 by the parent-sample sampling mechanism and then pipetted into a dilution cell 18 present on the dilution disk.

(2) Diluent Delivery Action

A liquid diluent is delivered from the diluent delivery mechanism 20 to the dilution cell 18 into which the parent sample 38 has been pipetted.

(3) Diluent/Sample Mixing Action The parent sample 38 and the diluent are stirred and mixed using the diluent/sample mixing mechanism 21.

(4) Diluted-Sample Sampling Action

The sample that has been diluted by stirring and mixing is suctioned by the diluted-sample sampling mechanism 22 and then pipetted into a reaction cell 36 present on a reaction disk 35.

As listed in Tables 1 and 2, parent-sample sampling action (1) is executed in the first cycle using a dilution cell (No. 1-A) of the dilution disk A 16. In the second cycle, the dilution disk A 16 rotates and diluent delivery action (2) and diluent/sample mixing action (3) are conducted in that order for the dilution cell (No. 1-A).

In the third to fourth cycles, the dilution disk A 16 rotates and diluted-sample sampling action (4) is conducted for the dilution cell (No. 1-A). In the fifth cycle, after the diluted-sample sampling action, the dilution disk A 16 rotates, and control moves to the next dilution process that uses an immediately next dilution cell (No. 30-A).

While the diluted sample is being pipetted in the third to fourth cycles using the dilution disk A 16, dilution process actions (1) to (3) are conducted on the dilution disk B 17 using a dilution cell (No. 1-B).

In the fifth cycle, after diluted-sample sampling on the dilution disk A 16, diluted-sample sampling action (4) is conducted for the dilution cell (No. 1-B). In the seventh cycle, after diluted-sample sampling action (4) for the dilution cell (No. 1-B), the dilution disk B 17 rotates, and control moves to the next dilution process that uses an immediately next dilution cell (No. 30-B).

In the fifth to sixth cycles, dilution process actions (1) to (3) are conducted on the dilution disk A 16 using a dilution cell (No. 30-A). In the seventh cycle, after diluted-sample sampling into the dilution cell (No. 1-B), control moves to the pipetting of the diluted sample into a dilution cell (No. 30-A).

Continuous dilution can be conducted in this manner by assigning a fixed delay in the execution timing of the dilution process between the two dilution disks. Since the dilution process is repeated for multiple dilution cells in succession, the total processing time can be reduced.

Before being reused, the dilution cell 18 is cleaned by the dilution cell cleaning mechanism A 23 and the dilution cell cleaning mechanism B 24. The dilution cell cleaning mechanism A 23 conducts a dilution cell cleaning action for the dilution disk A 16 while the parent-sample sampling mechanism 19 is accessing the dilution disk A 16. The dilution cell cleaning mechanism B 24 conducts a dilution cell cleaning action for the dilution disk B 17 while the diluted-sample sampling mechanism 22 is accessing the dilution disk B 17.

As listed in Tables 1 and 2, the two dilution disks continuously conduct the dilution process while using immediately next dilution cells. In this case, if one rotation cycle of the reaction disk 35 is seven seconds long, it takes 700 seconds (100 cycles) for a specific dilution cell to arrive at the dilution cell cleaning position after the diluted-sample sampling action.

A time of 600 seconds is usually required from completion of the diluted-sample sampling action to output of analytical results, and the dilution disk can hold the diluted sample for a time required for completion of confirming whether re-analysis for reasons such as an analytical error is necessary. If the re-analysis is necessary, the dilution disk is rotated and after the dilution cell containing the diluted sample has been moved to the diluted-sample suction position, the diluted-sample sampling action is immediately re-executed. The re-analysis can thus be conducted rapidly.

For analysis of hemoglobin "A1c", after the parent sample 38 has been diluted, there is a need to leave this diluted sample intact in the dilution cell for a fixed time until the diluted sample has been pipetted into the next dilution cell. For this analytical item, after dilution process actions (1) to (3) have been executed, diluted-sample sampling action (4) is skipped and the next dilution process is preferentially conducted. After a lapse of a necessary time, the dilution disk is rotated, then the dilution cell containing the diluted sample is moved to the diluted-sample suction position, and diluted-sample sampling action (4) is executed.

In the clinical automatic analyzer of the present invention that involves sample dilution using dilution disks, the layout of the parent-sample sampling mechanism, diluent delivery mechanism, diluent/sample mixing mechanism, and diluted-sample sampling mechanism used in the dilution process can be freely determined, which alleviates limitations on apparatus design.

What is claimed is:

1. An automatic analyzer comprising:

a reaction disk with reaction cells arrayed thereon;

a dilution disk with dilution cells annularly arrayed thereon;

a dilution disk rotating mechanism for rotating said dilution disk;

a parent-sample sampling mechanism configured to pipette a parent sample into the dilution cells from a sample container receiving a sample;

a diluent delivery mechanism configured to deliver a liquid diluent to the dilution cells having the parent sample pipetted thereinto;

a mixing mechanism for mixing the parent sample and the diluent pipetted into the dilution cells;

a diluted-sample sampling mechanism configured to pipette a diluted sample created by mixing the parent sample and the diluent in the dilution cells into the reaction cells;

a diluted sample analysis device configured to analyze diluted samples; and a controller configured to control the rotating mechanism for rotating said dilution disk, and to control an operation of the parent sample sampling mechanism, an operation of the diluent delivery mechanism, an operation of the mixing mechanism, and an operation of the diluted sample sampling mechanism to execute the operations at positions which are different from each other on the dilution disk, wherein the controller is configured to control the operations being executed successively by the parent sample sampling mechanism, the diluent delivery mechanism, the mixing mechanism, and the diluted sample sampling mechanism with respect to respective ones of said dilution cells on the dilution disk by temporarily stopping the rotating of the dilution disk rotating mechanism at the different positions, each of the operations being executed at a stop timing of the rotation of the dilution disk, wherein the controller is further configured to control analysis of the diluted sample analysis device to analyze diluted samples such that after analysis of a diluted sample, the dilution disk holds the diluted sample for a time it takes for completion of confirming whether re-analysis is necessary, and such that if the re-analysis is necessary, the dilution disk rotates and after the dilution cell containing the diluted sample has been moved to a diluted-sample suction position, the diluted-sample sampling is repeated;

two dilution disks that are rotated concentrically about a common axis by the rotating mechanism for rotating said dilution disk and wherein the two dilution disks are arranged with the dilution cells in two rows, one said row to form an inner peripheral region and an other said row to form an outer peripheral region, wherein the controller is further configured to control the rotation of the rotating mechanism for rotating said two dilution disks such that while said one dilution disk is being used for pipetting the diluted sample, the other dilution disk is used to execute said operations for parent-sample, diluent delivery, and diluent/sample mixing sequentially, and such that after the pipetting of the diluted sample using the said one dilution disk, the diluted sample is immediately pipetted from the other dilution disk.

2. The automatic analyzer according to claim 1, wherein the controller is further configured to control the diluted sample analysis device such that for an analytical item requiring analysis, after the diluted sample has been left intact in the dilution cell for a fixed time, the pipetting of the diluted sample is skipped for a fixed time and a next dilution process is preferentially conducted, and control the rotating mechanism for rotating said dilution disk such that after a lapse of a predetermined time, the dilution disk is rotated, and the dilution cell containing the diluted sample is moved to the diluted-sample suction position, and the diluted-sample sampling operation is executed.

* * * * *